United States Patent [19]

Lebeau et al.

[11] Patent Number: 5,246,291
[45] Date of Patent: Sep. 21, 1993

[54] BOND INSPECTION TECHNIQUE FOR A SEMICONDUCTOR CHIP

[75] Inventors: Christopher J. Lebeau, Tempe; Paul A. Ogden, Phoenix; Shay-Ping T. Wang, Tempe, all of Ariz.

[73] Assignee: Motorola, Inc., Schaumburg, Ill.

[21] Appl. No.: 891,002

[22] Filed: Jun. 1, 1992

[51] Int. Cl.⁵ ............................................. G01N 25/18
[52] U.S. Cl. ....................................... 374/5; 374/124; 374/137; 228/104
[58] Field of Search ..................... 374/4, 5, 124, 137; 228/103, 104

[56] References Cited

U.S. PATENT DOCUMENTS

| | | | |
|---|---|---|---|
| 3,803,413 | 4/1974 | Vanzetti et al. | 250/338.1 |
| 4,792,683 | 12/1988 | Chang et al. | 250/341 |
| 4,999,499 | 3/1991 | Bhatt | 250/342 |
| 5,052,816 | 10/1991 | Nakamura et al. | 374/5 |
| 5,064,291 | 11/1991 | Reiser | 356/372 |

FOREIGN PATENT DOCUMENTS

| | | | |
|---|---|---|---|
| 142427 | 11/1981 | Japan. | |
| 0127660 | 5/1987 | Japan | 374/4 |
| 0126339 | 6/1987 | Japan | 374/4 |
| 0282770 | 12/1987 | Japan | 228/104 |

Primary Examiner—William A. Cuchlinski, Jr.
Assistant Examiner—W. Morris Worth
Attorney, Agent, or Firm—Joe E. Barbee

[57] ABSTRACT

A bond inspection technique which determines the integrity of a plurality of package leads (13) bonded to a plurality of contact areas (12) on a semiconductor chip (11). A bonding process heats each package lead (13) bonded to each contact area (12). A camera (16) forms an infra-red intensity image at a predetermined time of the semiconductor chip (11) and ports image data to a computer (18). Infra-red intensity radiated from each bond on the semiconductor chip (11) is compared by the computer (18) with infra-red intensity data of known good and bad bonds. The comparison of each bond determines bond integrity of the semiconductor chip (11).

16 Claims, 1 Drawing Sheet

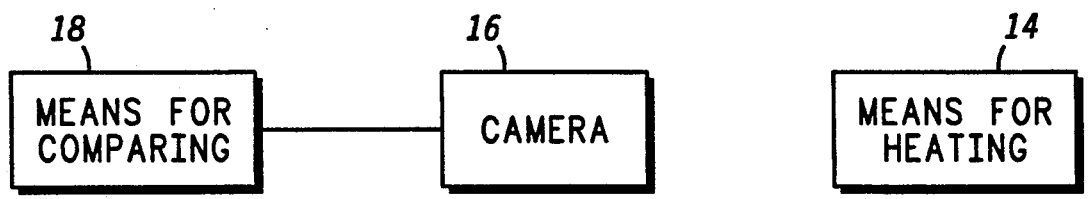
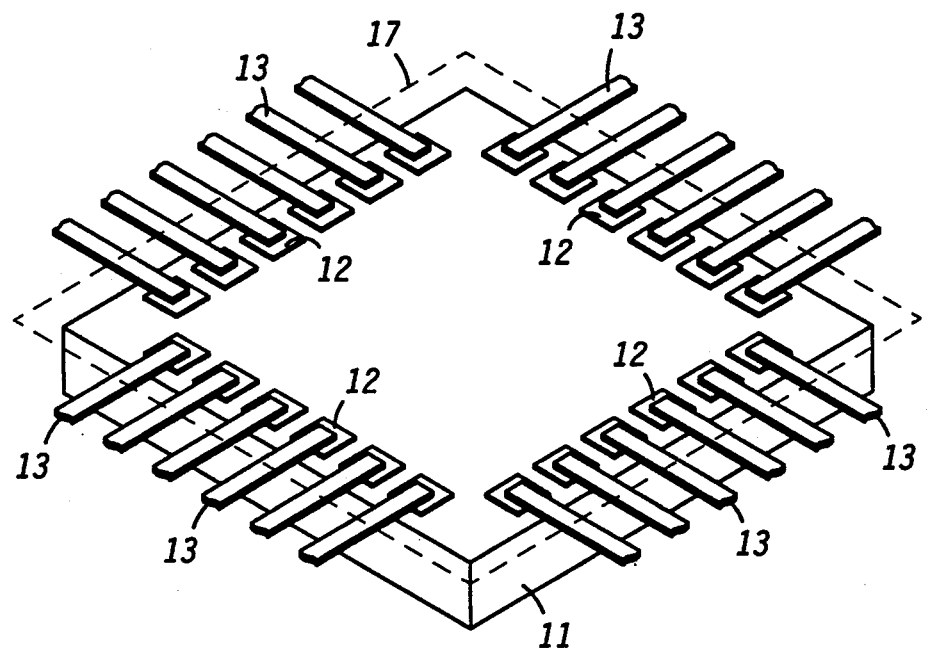

BOND INSPECTION TECHNIQUE FOR A SEMICONDUCTOR CHIP

BACKGROUND OF THE INVENTION

This invention relates, in general, to package lead bond inspection for semiconductor chips, and more particularly to bond inspection techniques which can evaluate all bonds on a semiconductor chip simultaneously.

Pin counts for semiconductor chips are increasing at a fantastic rate. New package techniques are emerging to handle pin counts ranging from 256 pins to over several thousand pins. Package interconnects or package leads which contact a semiconductor chip must be extremely small and tightly spaced to accommodate these large numbers. Package leads are bonded to a contact pad on the semiconductor chip to insure electrical connection from the semiconductor chip to the package lead. Knowledge of the integrity of each bond on a semiconductor chip is essential to cull out bad parts and to eliminate parts which may have package lead bonds that may fail or cause intermittent problems over the lifetime of the semiconductor chip due to vibration or some other failure mechanism.

Current test strategies for evaluating bonds do not adequately meet quality, test throughput, and long term reliability issues involved with high pin count semiconductor chips. Tests commonly used include visual inspection, electric continuity, and destructive tests. For example, a TAB package may have several hundred package leads connected to a semiconductor chip. The package leads are very small and tightly spaced. A visual inspection may turn up only gross defects in the bonding process and will not determine the electrical characteristics of each package lead to semiconductor chip bond. An electric continuity test proves a connection exists between a package lead and the semiconductor chip but may not show high current problems with the connection or long term problems which could develop due to a poor bond. Long term testing under high current or high stress conditions is a solution to this problem but is very costly. A destructive test is a test through sampling. The quality of a package lead bond can be determined by physically pulling a package lead from the semiconductor device. The higher the force needed to pull a package lead from a semiconductor chip the stronger the bond. This test destroys the bond which is tested, thus it is a destructive test, the results of the destructive test are used to infer whether other bonds on the semiconductor chip are good. The destructive test assumes other bonds on the semiconductor chip are formed similarly to the bond destroyed in the test. A random sampling using the destructive test will not adequately determine the integrity of all bonds on the semiconductor chip as pin counts increase and package lead spacings are made smaller. Even using all three of these tests may not meet quality standards set up by semiconductor chip manufacturers.

It would be of great benefit if a technique for testing a high pin count semiconductor chip can be developed which rapidly evaluates all package lead to semiconductor chip bonds, determines bond current handling capability, and is easily automated with existing equipment.

SUMMARY OF THE INVENTION

Briefly stated, this invention is a package lead bond integrity test for semiconductor chips. A means for sensing infra-red radiation is used to generate a thermal intensity map of a semiconductor chip. Thermal conductivity through each bond area can be determined from the thermal intensity map. A means for comparing intensity and location data is used to determine bond quality on the semiconductor chip. The means for comparing compares the semiconductor chip thermal intensity map with data from substantially similar semiconductor chips with known bond integrity.

BRIEF DESCRIPTION OF THE DRAWINGS

The single figure is an illustration of a plurality of bonds being tested in accordance with the present invention.

DETAILED DESCRIPTION OF THE DRAWINGS

The single figure illustrates the technique for evaluating a plurality of bonds on a semiconductor chip 11. A plurality of package leads from a semiconductor chip package are bonded to semiconductor die 11. Each package lead 13 has a corresponding contact area 12 on semiconductor die 11 in which a bond is formed. The number of bonds shown on the semiconductor chip is for illustration purposes only, bonds can number from one to over a thousand bonds.

In the preferred embodiment, contact areas 12 and package leads 13 are made of a conductive material to transfer signals from the semiconductor chip 11 to components external to the semiconductor chip package. The bond between a contact area 12 and a package lead 13 has physical and electrical properties which are characterized in the technique for bond evaluation. Physically, a bond must not fatigue or break with age due to environmental factors such as vibration, temperature variations, or humidity. Electrically, signals from semiconductor chip 11 must be transferred from a signal line to a contact area, through a bond, and a package lead with little or no signal degradation. The bond can affect the resistance of the signal path and limit current handling capacity.

The physical and electrical properties of a bond have one common element which can be exploited to create a test which can be used to rapidly evaluate a plurality of bonds. Both the physical and electrical integrity of a bond can be related to the total surface area at the bond interface between contact area 12 and package lead 13. A bond having more surface area at the bond interface when compared to another bond (formed under substantially similar conditions) will be physically a stronger bond and have a lower resistance.

The bond inspection technique for a semiconductor chip uses heat transfer to determine bond interface area, and thus bond quality. A laser 14 serves as a means for heating. Laser 14 is used to heat plurality of package leads 13 near each bond interface formed by a package lead 13 bonded to a contact area 12. Laser 14 can rapidly and accurately heat substantially similar areas of each package lead to provide uniform results when evaluating all bonds on semiconductor chip 11 simultaneously. In the preferred embodiment, heat from the bonding process itself is used to determine bond integrity which eliminates the need for laser 14. Since all bonds between package leads 13 and contact areas 12 are formed simultaneously during a bonding process, the bonds are by default at substantially similar temperatures.

Semiconductor chip 11 acts as a heat sink to dissipate heat from a bond. Heat stored in a package lead and bond dissipate through a path of least resistance. This path is through the bond interface and contact area 12 to semiconductor chip 11. The main restriction through this path is the bond interface area. How quickly heat is transferred to semiconductor chip 11 is determined by the bond interface area. Each bond will be transferring heat to semiconductor chip 11 simultaneously.

A camera 16 for sensing infra-red radiation is used to measure infra-red radiation radiated from semiconductor chip 11. Camera 16 serves as a means for sensing infra-red radiation. In the preferred embodiment, camera 16 is a CCD camera which is sensitive to the infra-red spectrum of light. CCD camera 16 has an inexpensive purchase price when compared with cameras designed specifically for infra-red sensing. If CCD camera 16 has an infra-red filter, it must be removed to sense the infra-red spectrum of light. CCD camera 16 is placed above semiconductor die 11. The field of view of CCD camera 16 when focused on semiconductor chip 11 is illustrated by dotted line 17 and will view (at a minimum) portions of plurality of package leads 13 and all of semiconductor chip 11 (which includes each package lead 13 to contact area 12 bond). CCD camera 16 will output X and Y coordinate information within its field of view at a predetermined time. Each X and Y coordinate within CCD camera 16 field of view has an infra-red intensity measurement associated with it. A thermal intensity map or infra-red intensity image is constructed of semiconductor chip 11 from the information output from the CCD camera 16 illustrating radiated infra-red intensity.

As mentioned previously, in the preferred embodiment, the bonding process heats each package lead 3, each bond interface, and each contact area. Initially, each bond is heated to substantially similar temperatures when forming the bonds. The resultant thermal image from CCD camera 16 at this time would result in a thermal image of semiconductor chip 11, wherein each location where a bond existed would image similar infra-red radiated intensity. After a period of time, each bond transfers heat from the bond to semiconductor chip 11. The rate at which heat can be transferred from the bond to semiconductor chip 11 is a function of the bond interface area. A thermal image of semiconductor chip 11 is taken by CCD camera 16 at a predetermined time after the bonding process. The thermal image taken at the predetermined time will determine good and bad bonds. Good bonds will dissipate heat faster than bad bonds due to increased area at the bond interface in which to transfer heat to semiconductor chip 11. Conversely, bad bonds retain heat longer and would image a higher radiated intensity at the predetermined time.

The simplicity of the bond inspection technique lies in the fact that absolute temperatures of each bond are not measured, only the intensity of radiated infra-red as imaged by CCD camera 16. Typical CCD cameras have a resolution of 8 bits in which to quantify radiated infra-red intensity, this is more than adequate for a bond evaluation application. The emitted intensity of each bond on semiconductor chip 11 is contained in a single image from CCD camera 16. This allows very rapid throughput when inspecting bond integrity in a production environment.

Prior to actual bond testing, substantially similar semiconductor chips are characterized under similar conditions as semiconductor chip 11. Infra-red intensity data of each bond taken by CCD camera 16 is correlated to the actual condition of each bond on the substantially similar semiconductor chips. A destructive test is one method used to determine the actual condition of bonds on the substantially similar semiconductor chips. The data collected from actual bond conditions is used to determine a range of acceptable infra-red intensity levels emitted from a bond which correspond to a good bond. The acceptable infra-red intensity levels and the location of each bond on semiconductor chip 11 are stored in a computer 18 which serves as a means for comparing intensity and location data.

In a production environment, bond evaluation must occur as rapidly as possible to minimize costs of testing. In the preferred embodiment, testing bond integrity during the bonding process is extremely cost effective. No additional set up is needed other than mounting CCD camera 16, heat from the bonding process is used which eliminates the need for an external heat source, a single infra-red intensity image is taken by CCD camera 16 of a semiconductor die at a predetermined time after the bonding process, and the data from CCD camera 16 is ported to computer 18. This sequence is easily automated within a standard bonding procedure and allows all bonds on a semiconductor die to be evaluated simultaneously. Computer 18 has location data of each bond and compares each bond infra-red intensity output with the acceptable infra-red intensity levels. Computer will determine if all bonds on a semiconductor die are acceptable, bad parts are culled out. Computer 18 can also be used to store statistical information of the bonding process which can be used to make changes to a bonding process to reduce the number of bad bonds.

An alternate approach to the bond inspection technique is to take a plurality of infra-red intensity images (or thermal maps) of semiconductor die 11, each at a predetermined time after the bonding process. The plurality of infra-red intensity images are used to show a rate of change of infra-red intensity at each bond, which indicates how well each bond transfers heat to semiconductor chip 11. The faster the rate of change the more surface area in the bond, thus a stronger bond. This technique can be used with an identical setup as previously discussed, only more time is needed to take the plurality of images.

By now it should be appreciated that a bond inspection technique for a semiconductor chip has been shown which increases the accuracy and speed in which plurality of package leads 13 bonded to plurality of contact areas 12 on semiconductor chip 11 can be tested. Heat transfer through a bond is an accurate means for determining total surface area at a bond interface. Surface area of a bond can be related to the physical strength of a bond and the electrical characteristics of the bond. CCD camera 16 is capable of generating an infra-red intensity image or thermal map of an entire semiconductor chip. Since a single infra-red intensity image is produced to test all bonds on semiconductor chip 11, the test can be performed quickly and inexpensively. The infra-red intensity image from CCD camera 16 can be ported to computer 18 as data. The data consists of X and Y coordinate location data with an infra-red intensity level associated with the X and Y coordinate location data. Infra-red intensity readings from each bond on semiconductor chip 11 are compared with known good and bad bond intensity readings. Computer 18 can rapidly process the data and respond to the integrity of bonds on semiconductor chip 11.

We claim:

1. A bond inspection technique for evaluating the bond interface between a plurality of leads bonded to respective contact pads on a semiconductor chip, comprising:

initially heating the plurality of leads and bond interfaces to allow heat across the bond interfaces between the leads and the contact pads to be dissipated via the contact pads to the semiconductor chip;

producing at least one thermal intensity map of the semiconductor chip using a camera sensitive to infra-red radiation, said at least one thermal intensity map being indicative of the heat transferred through the bond interfaces wherein the heat transfer is a function of the integrity of the bond interface itself; and inspecting said at least one thermal intensity map and comparing it against similar data at known good bond interfaces of a similar semiconductor chip to determine the quality of the bond interfaces of the semiconductor chip being evaluated.

2. The bond inspection technique of claim 1 wherein each bond to be evaluated on the semiconductor chip is heated to substantially similar temperatures.

3. The bond inspection technique of claim 1, wherein heating is by a laser and wherein each bond to be evaluated on the semiconductor chip is heated to substantially similar temperatures.

4. The bond inspection technique of claim 1, wherein a CCD camera is used having any infra-red filter removed from said CCD camera.

5. The bond inspection technique of claim 1, further including producing a plurality of thermal intensity maps using said camera, each thermal intensity map being generated at a different predetermined time to show a rate of change in heat transfer through each bond.

6. A method for simultaneously characterizing a plurality of package lead bonds on a semiconductor chip comprising:

initially heating a plurality of package leads and their respective bonds on the semiconductor chip for a predetermined time;

placing the plurality of package leads and the semiconductor package in the field of view of a camera sensitive to infra-red radiation;

generating a thermal intensity map of said plurality of package lead bonds and the semiconductor chip as heat is transferred therebetween from data output by said camera, said thermal intensity map indicating the heat transferred through each bond interface between said plurality of package leads and the semiconductor chip; and comparing said thermal intensity map to data of substantially similar semiconductor chips with known package lead bond conditions.

7. The method of claim 6 wherein initial heating comprises using heat generated during a bonding process for bonding the plurality of leads to the semiconductor chip to promote heat transfer through each bond interface.

8. The method of claim 6 wherein initial heating comprises:

heating an area of the package leads near each bond interface with a laser to promote heat transfer through each bond interface.

9. The method of claim 6 further including:

using a CCD camera with infra-red filters removed as said camera.

10. The method of claim 6 wherein the step of comparing comprises:

comparing said thermal intensity map to data of substantially similar semiconductor chips with known bond conditions using a computer.

11. The method of claim 6 further including:

generating a plurality of thermal intensity maps of the semiconductor chip from data output by said camera, each thermal intensity map being generated at a predetermined time; using said plurality of thermal intensity maps to show a rate of change of thermal intensity at each bond;

and using said rate of change thermal intensity at each bond to determine bond quality.

12. A method for inspecting the integrity of a plurality of package leads bonded to a semiconductor chip, comprising:

focusing a camera sensitive to infra-red radiation on the plurality of package leads and the semiconductor chip;

causing heat transfer through each bond interface between the plurality of leads and the semiconductor chip;

generating a thermal intensity map of the semiconductor chip and leads fro data output from said camera, said thermal intensity map showing heat transferred through each bond interface; and inspecting and comparing said thermal intensity map against substantially similar semiconductor chip data with known package lead bond conditions.

13. The method of claim 12 wherein said causing heat transfer step includes using heat generated during a package lead bonding process to cause heat transfer through each bond interface.

14. The method of claim 12 wherein said causing heat transfer step includes heating an area of the plurality of package leads near each bond with a laser to cause heat transfer through each bond interface.

15. The method of claim 12 wherein said generating a thermal intensity map step includes generating a plurality of thermal intensity maps at predetermined times to determine a rate of change of heat transfer through each bond interface.

16. The method of claim 12 wherein said comparing and inspecting step includes using a computer to compare said thermal intensity map to substantially similar semiconductor chip data with known package lead bond conditions.

* * * * *